(12) United States Patent
Jin

(10) Patent No.: US 6,776,165 B2
(45) Date of Patent: Aug. 17, 2004

(54) MAGNETIC NAVIGATION SYSTEM FOR DIAGNOSIS, BIOPSY AND DRUG DELIVERY VEHICLES

(75) Inventor: Sungho Jin, San Diego, CA (US)

(73) Assignee: The Regents of the University of California, San Diego, CA (US)

( * ) Notice: Subject to any disclaimer, the term of this patent is extended or adjusted under 35 U.S.C. 154(b) by 40 days.

(21) Appl. No.: 10/242,389

(22) Filed: Sep. 12, 2002

(65) Prior Publication Data

US 2004/0050394 A1 Mar. 18, 2004

(51) Int. Cl.[7] .............................. A61B 19/00; A61B 5/05
(52) U.S. Cl. ...................................... 128/899; 600/424
(58) Field of Search ............................... 600/114, 117, 600/407, 109, 101, 587, 424, 300, 474, 486, 426, 582, 302, 549, 578, 106; 324/507.1; 606/41, 130; 128/899, 903; 396/17, 183; 348/77, 76, 92; 455/100, 67.11, 67.13, 95; 604/113, 890.1, 891.1, 131, 327, 93.01, 244; 424/426

(56) References Cited

U.S. PATENT DOCUMENTS

| | | | | | |
|---|---|---|---|---|---|
| 4,278,077 A | * | 7/1981 | Mizumoto | ................... | 600/109 |
| 4,425,117 A | * | 1/1984 | Hugemann et al. | ......... | 604/244 |
| 4,507,115 A | * | 3/1985 | Kambara et al. | ........... | 604/135 |
| 4,844,076 A | * | 7/1989 | Lesho et al. | ................ | 600/302 |
| 5,170,801 A | * | 12/1992 | Casper et al. | ................ | 600/582 |
| 5,217,449 A | * | 6/1993 | Yuda et al. | .............. | 604/890.1 |
| 5,267,033 A | * | 11/1993 | Hoshino | ....................... | 348/92 |
| 5,279,607 A | * | 1/1994 | Schentag et al. | ......... | 604/890.1 |
| 5,415,181 A | * | 5/1995 | Hogrefe et al. | ............. | 600/549 |
| 5,604,531 A | * | 2/1997 | Iddan et al. | .................. | 348/76 |
| 5,681,260 A | * | 10/1997 | Ueda et al. | ................. | 600/114 |
| 5,916,584 A | * | 6/1999 | O'Donoghue et al. | ...... | 424/426 |
| 5,925,030 A | * | 7/1999 | Gross et al. | ............. | 604/890.1 |
| 6,240,312 B1 | * | 5/2001 | Alfano et al. | ............... | 600/476 |
| 6,428,469 B1 | * | 8/2002 | Iddan et al. | ................ | 600/109 |
| 6,632,171 B2 | * | 10/2003 | Iddan et al. | ................ | 600/106 |
| 6,690,963 B2 | * | 2/2004 | Ben-Haim et al. | .......... | 600/424 |
| 2002/0099310 A1 | * | 7/2002 | Kimchy et al. | ............. | 600/587 |
| 2003/0167000 A1 | * | 9/2003 | Mullick et al. | ............. | 600/424 |
| 2003/0208107 A1 | * | 11/2003 | Rafael | ........................ | 600/300 |

\* cited by examiner

*Primary Examiner*—Mary Beth Jones
*Assistant Examiner*—Nikita R Veniaminov
(74) *Attorney, Agent, or Firm*—Lowenstein Sandler PC

(57) ABSTRACT

This invention discloses such a convenient navigation system and navigatable capsules which are useful for remote-controlled imaging, biopsy and programmable drug release within the body of an animal. The components of the system comprise a capsule dimensioned and shaped to move within the body. An anisotropic magnetic component is mechanically coupled to the capsule to move or orient the body in relation to an applied magnetic field, and a magnetic field generating system external of the body generates a three dimensionally oriented magnetic field within the body to move or orient capsule.

15 Claims, 3 Drawing Sheets

MAGNETIC NAVIGATION SYSTEM FOR DIAGNOSIS, BIOPSY AND DRUG DELIVERY VEHICLES

FIELD OF INVENTION

This invention relates to bioengineering systems, and in particular, to a magnetic navigation system for moving a device within the body of an animal such as a human being. The system is particularly useful within tracts, ducts or cavities such as the gastrointestinal (GI) tract.

BACKGROUND OF INVENTION

Various diagnostic techniques are used for detection of tumors, ulcers, and other abnormal conditions in the body. These techniques include x-ray imaging, ultrasonic testing, MRI, endoscopy, sigmoidoscopy and colonoscopy. Recently, a camera-in-a-capsule device has been developed and reported, see U.S. Pat. No. 5,604,531, "In vivo video camera system" issued to Iddan et al. on Feb. 18, 1997 and U.S. Pat. No. 6,428,469, "Energy management of a video capsule" issued to Iddan et al. on Aug. 6, 2002. Recent FDA approval (August, 2001) of an ingestible camera developed by Given Imaging Ltd. and tested at New York Mount Sinai Hospital received considerable news media attention. Such a device is schematically illustrated in FIGS. 1 and 2.

Referring to FIGS. 1 and 2, the ingestible camera 10 is a finger-tip sized capsule 11 containing a camera composed of lens 12, an image detector 13 and one or more light sources 14. A wireless transmitter 15 (including antenna) is provided for video signal transmission. The capsule also includes, batteries 16, and circuit chips (not shown). When a patient swallows the capsule, the natural muscular waves of the digestive tract propel it downward; and, as it goes down, the camera takes pictures of the small intestine wall for video transmission to detect tumors, ulcers, or causes of bleeding. This procedure permits the diagnosis of the small intestine, which is difficult to access by colonoscopy. For larger regions, such as the stomach or the large intestine, this type of non-guided camera tends to lose orientation and reliable imaging covering all surface areas is no longer be possible. It would be desirable if the position of the camera could be controlled so that no portion of the GI tract surface would be missed.

The most common therapy for treatment of GI tract problems with drugs is oral administration, rather than a concentrated application of the drugs directly on the affected area. Such a practice results in inefficient use of drugs, and is often accompanied by unwanted side-effects, with restrictions in the use of more potent treatment doses, especially in the treatment of tumors. It would be highly desirable if the drug release can be programmed so that the exact desired doses can be applied directly at a time at a specific location in the GI tract (e.g., on or near a tumor). Accordingly there is a need for a system to direct the movement and orientation of diagnosis and treatment vehicles within animal bodies.

SUMMARY OF THE INVENTION

This invention discloses such a convenient navigation system and navigatable capsules which are useful for remote-controlled imaging, biopsy and programmable drug release within the body of an animal. The components of the system comprise a capsule dimensioned and shaped to move within the body. An anisotropic magnetic component is mechanically coupled to the capsule to move or orient the body in relation to an applied magnetic field, and a magnetic field generating system external of the body generates a three dimensionally oriented magnetic field within the body to move or orient capsule.

BRIEF DESCRIPTION OF THE DRAWINGS

The nature, advantages and various additional features of the invention will appear more fully upon consideration of the illustrative embodiments now to be described in detail with the accompanying drawings. In the drawings.

It is to be understood that the drawings are for purposes of illustrating the concepts of the invention and are not to scale.

DETAILED DESCRIPTION OF THE INVENTION

In order to solve the operation difficulties and limitations associated with non-guided drug release capsules or diagnostic capsules, a new, remote-controlled, magnetic navigation system is provided to efficiently guide diagnostic or medication capsules within the body and perform diagnostic, biopsy or programmable drug release. Within the GI tract, the navigatable capsules override the time limit imposed by the naturally occurring muscular movement of the tract, thus allowing repeated medication therapy on one or more affected areas over an extended period of time.

Figure 1:
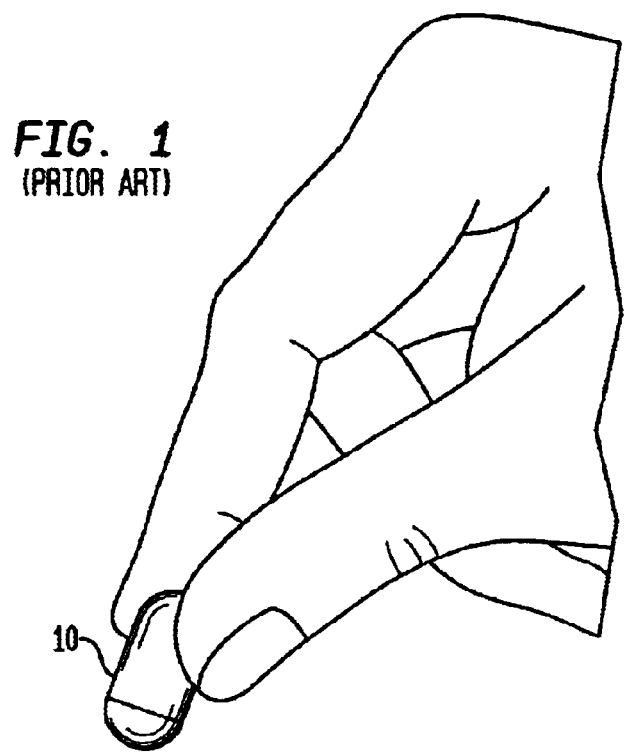
FIG. 1, which is prior art, depicts a swallowable camera.
Figure 2:
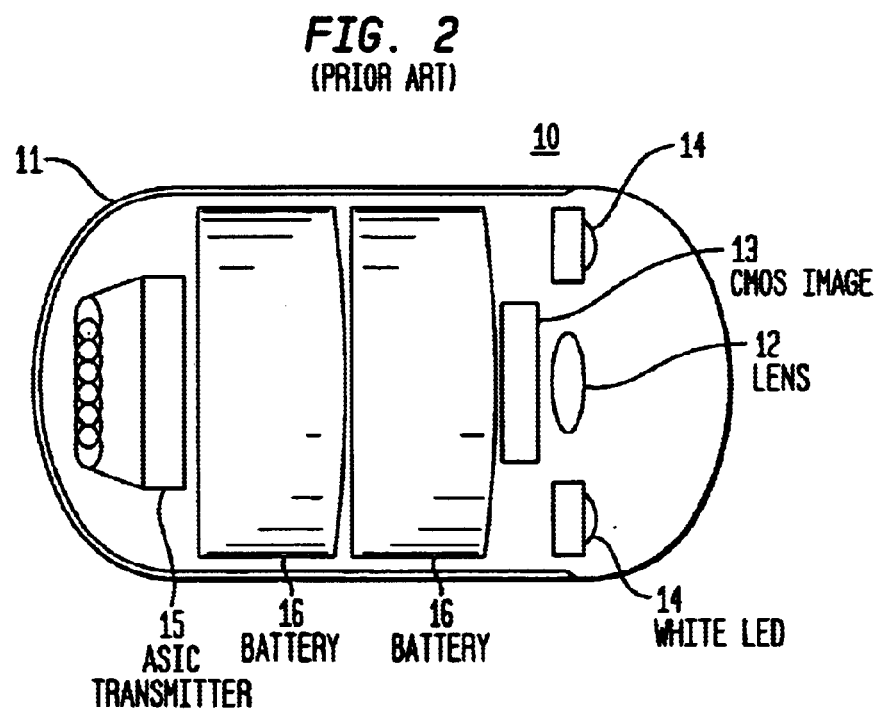
FIG. 2, which is prior art, schematically illustrates the components of the FIG. 1 device.
Figure 3:
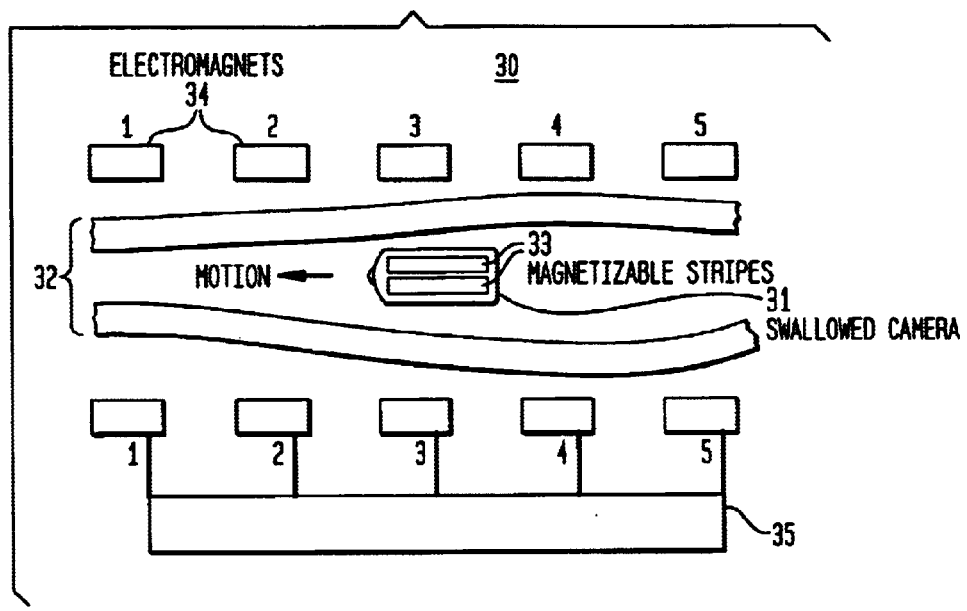
FIG. 3 schematically illustrates an exemplary navigatable biocapsule device and navigation control system according to the invention.

FIG. 3 schematically illustrates a system 30 for moving a capsule 31 within the body of an animal 32 to accomplish magnetic navigation of the capsule 31, one or more soft magnetic, semi-hard magnetic, or permanent magnetic component is mechanically coupled to the capsule, e.g. embedded inside the capsule or attached onto the surface. In the case of surface-mounted magnetic component, it is preferably coated with biocompatible, clinically safe material (not shown) such as, for example, diamond, a bio-compatible polymer, titanium, or stainless steel. A magnetic component 33 should be anisotropic either in magnetic properties or in shape to orient the capsule in relation a magnetic field applied by electromagnets 34. The shape of the magnetic component should be elongated along the length direction of the capsule to provide magnetic shape anisotropy or the component can comprise a material with high magneto-crystalline anisotropy along the length direction. In the presence of three-dimensional guiding field, the anisotropy aligns the capsule along the direction of the applied field. By slowly altering the applied field direction following the contour of a tract or duct, the capsule can be guided along the tract or duct, e.g. along the GI tract. A three-dimensional, programmable magnetic field system made up of a series of electromagnets, superconducting magnets, or movable permanent magnets, can externally generate a guiding magnetic field within the body. Each electromagnet 34 can be separately controlled by a processor 35 to establish a field of desired magnitude, orientation and gradient in the region of capsule 31.

Movement of the magnetic object is induced if there is a magnetic field gradient near the magnetic object. A programmable or sequential change of electromagnets 34 can provide a magnetic field strength and gradient near the magnetically tagged capsule to guide and move the capsule at a programmed speed. The capsule 31 is dimensioned and shaped to move within a tract, duct or cavity of the body.

The exemplary capsule 31 shown as a camera for video imaging. However, the present invention also includes other navigatable devices such as a biopsy device, a drug release device, or a diagnostic or treatment device, or any combination of these. The navigatable diagnostic and/or theraputic treatment devices can include, for example, a local ultrasonic wave source and/or detector for localized acoustic diagnosis or treatment (e.g., to damage or disrupt unwanted cell structure), a localized x-ray source and/or detector, a source of intense heat radiation to disrupt or damage tumor growth, or a mechanical vibration source and/or detector to stimulate or slow down cell growth.

While the gradient along the GI tract direction needs to be maximized for capsule movement, the gradient along the perpendicular directions should be balanced to prevent undue pressure on the GI tract wall. An array of biocompatible pressure sensors (not shown) can be embedded on the capsule surface so that the sensed pressure information is transmitted as a feedback to the programmable 3-D field generation system. In response to the pressure signals the magnetic field distribution can be automatically adjusted to eliminate the sideways pressure.

The position of the capsule 31, if needed to be traced in real time, may be detected by a number of different tracking techniques. For example, magnetic interrogation (magnetic position sensing), ultrasound imaging, or CT scan may be utilized. Feedback to the 3-D field generation system can be used to obtain desired movement.

Figure 4A:
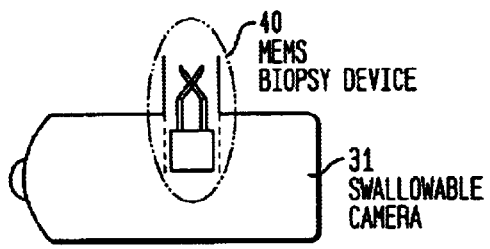
FIGS. 4(a) and (b) schematically illustrate exemplary magnetically navigatable biopsy MEMS devices according to the invention.

Recent advances in MEMS (Micro-Electro-Mechanicalsystems) technology now permit fabrication of very minute machines capable of complex motions and maneuvers. A bioMEMS device can be incorporated into the magnetically navigatable capsule to perform tissue sampling (e.g., for biopsy of polyps, tumor cells) or body fluid sampling in the tract, duct or cavity. Such a device is schematically illustrated in FIG. 4A. A pop-up instrument 40 collects the tissue sample and then retracts into the capsule with a door closing behind. Such a command for biopsy action can be relayed to the MEMS capsule by remote magnetic signals or wireless RF signals. Alternatively, a fluid sample door can be opened and closed upon command.

Figure 4B:
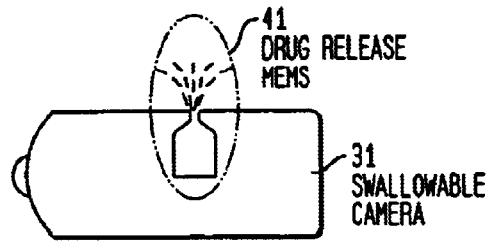
Figure 5:
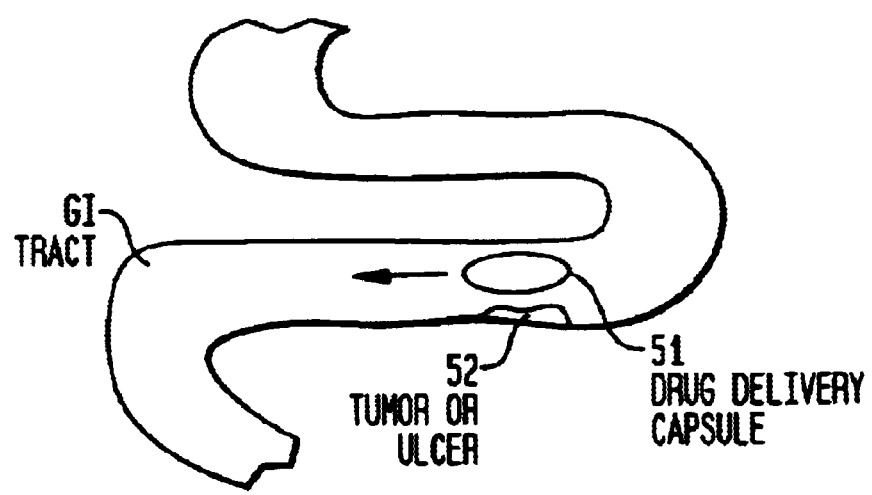
FIG. 5 schematically illustrates an exemplary use of navigatable, programmable, and remote-releasable drug release MEMS capsule according to the invention.

The MEMS capsule can also be made with a drug release compartment 41 to store and programmably release desired medications (FIG. 4B) such as chemotherapy drugs or antibiotics as schematically illustrated in FIG. 5, a drug delivery capsule 51 can controllably release directly on a problem area 52. The magnetically navigatable system enables the capsule to stay at a fixed location and release medication repeatedly over extended period, for example, every 4 hours. If there are two tumors to be treated, the capsule can go back and forth and release the drug on both areas repeatedly. If a mix of drugs is to be administered, a MEMS capsule with a multi-compartment structure will be commanded to do so via remote signals. The programmable drug release device, according to the invention, contains remote-activatable valves and other actuation mechanisms which can be activated by either magnetic means or by FM/microwave signals (if the use of magnetic actuation is undesirable or is to be minimized). For example, an activation/operation of remote magnetic release of valves in the drug release capsule may be affected by the presence of navigating magnetic field unless the navigating field is temporarily turned off for short time drug release. In case of prolonged holding of the navigating capsule in place by magnetic field, the field can not be turned off during the intended period.

The capsule can be powered with a battery, for example, typically with several hours life. Alternatively, the system can be provided with an AC magnetic field source (e.g. 60 Hz) and the navigating biocapsule can be equipped with a transducer device for receiving energy through the external AC magnetic field. Using a magnetic AC induction coupling, a transformer solenoid in the capsule can receive power from outside, and then convert the AC power to DC power and store the energy in the battery or a capacitor. This embodiment indefinitely extends the battery life, and the useful life of the device.

In summary, it can now be seen that the invention includes a system for moving a capsule within the body of an animal. (The term animal as used herein is intended to include human beings). The components of the system comprise a capsule dimensioned and shaped to move within the body of the animal. An anisotropic magnetic component is mechanically coupled to the capsule to move or orient the capsule in relation to an applied magnetic field, and a magnetic field generating system external of the body is provided for generating a three dimensionally oriented magnetic field within the body to move or orient the capsule. Advantageously the capsule has an outer surface of biologically compatible (biocompatible) material. And in a preferred embodiment the system includes a detector for determining the location or orientation of the capsule within the body. The detector can be selected, for example, from devices utilizing a number of different techniques such as x-ray analysis, ultrasonic sensing, magnetic position sensing. The programmable magnetic field generator can then respond to the detected location of the capsule to orient the capsule at a desired orientation for the detected location. The position of the capsule can be continuously detected, and the feedback of the position information can be used to control the magnetic navigation system in guiding or moving the capsule. The pressure on the sidewalls of the capsule can be continuously detected by sensors on the capsule, and the feedback of the pressure information can be used to control the system to minimize pressure on the wall of the tract, duct or cavity.

In advantageous embodiments, the capsule can be dimensioned and shaped for moving in a tract, duct or cavity of the body, e.g. an elongated capsule is convenient for moving in the gastro-intestinal tract. It can include an imaging device, a biopsy device, a drug release device or a source or detector of ultrasonic energy, thermal energy or mechanical vibration for treatment or diagnosis. A spherically symmetrical capsule may be advantageous in cavities, and smaller capsules are preferred for smaller tracts and ducts. The sources can be remotely (externally) actuable. In addition, the capsule can be provided with a transducer for extracting energy from an externally generated AC magnetic field.

It is understood that the above-described embodiments are illustrative of only a few of the many possible specific embodiments, which can represent applications of the invention. Numerous and varied other arrangements can be made by those skilled in the art without departing from the spirit and scope of the invention.

What is claimed is:

1. A system for moving a capsule within the body of an animal comprising:
   a capsule dimensioned and shaped to move within the body of the animal;
   mechanically coupled to the capsule, an anisotropic magnetic component to orient the capsule in relation to an applied magnetic field;
   a detector to determine the location of the capsule within the body; and
   a magnetic field generating system external of the body responsive to the detected location of the capsule for generating a three dimensionally oriented field within the body to move the anisotropic magnetic component and thereby the capsule within the body.

2. The system of claim 1 wherein the detector senses the position of the capsule and the feedback of the position information at every moment is utilized for controlling the magnetic field generating system to guide the capsule.

3. The system of claim 1 wherein the detector senses sidewall pressure and the feedback of the pressure information is utilized by the magnetic field generating system to minimize the pressure exerted by the capsule on the wall of the tract duct or cavity.

4. The system of claim 1 wherein the capsule is dimensioned and shaped to move within the gastro-intestinal tract of an animal.

5. The system of claim 1 wherein the capsule includes an imaging device.

6. The system of claim 1 wherein the capsule includes a biopsy device.

7. The system of claim 6 wherein the biopsy device is remotely controllable.

8. The system of claim 1 wherein the capsule includes a drug release device.

9. The system of claim 8 wherein the drug release device is remotely controllable.

10. The system of claim 1 wherein the capsule includes a source or detector of ultrasonic energy.

11. The system of claim 10 wherein the source or detector of ultrasonic energy is remotely actuable.

12. The system of claim 1 wherein the capsule includes a source or detector of thermal energy.

13. The system of claim 12 wherein the source or detector of thermal energy is remotely actuable.

14. The system of claim 1 wherein the capsule includes a source or detector of mechanical vibration.

15. The system of claim 1 wherein the source or detector of mechanical vibration is remotely actuable.

* * * * *